United States Patent [19]

Pearce

[11] Patent Number: 4,903,826
[45] Date of Patent: Feb. 27, 1990

[54] DISPENSER FOR SURGICAL GUIDEWIRE

[75] Inventor: Harold J. Pearce, Tetbury, England

[73] Assignee: EMS Medical Group Ltd., Unit 3, Stonehouse, United Kingdom

[21] Appl. No.: 306,819

[22] Filed: Feb. 3, 1989

[30] Foreign Application Priority Data

Feb. 9, 1988 [GB] United Kingdom ............... 8802935

[51] Int. Cl.⁴ ................................................ A61B 17/06
[52] U.S. Cl. .................................. 206/63.3; 206/403; 206/409; 242/96; 242/171
[58] Field of Search ............... 206/63.3, 403, 409, 206/438, 303; 242/170, 171, 96

[56] References Cited

U.S. PATENT DOCUMENTS

| | | |
|---|---|---|
| 3,301,393 | 1/1967 | Regan, Jr. et al. ............... 206/63.3 |
| 3,338,401 | 8/1967 | Regan, Jr. ........................ 206/63.3 |
| 3,495,703 | 2/1970 | Calabrese ........................ 206/63.3 |
| 3,545,608 | 12/1970 | Berger et al. .................... 206/63.3 |
| 3,972,418 | 8/1976 | Schuler et al. ................... 206/63.3 |
| 4,084,692 | 4/1978 | Bilweis ............................ 206/403 |
| 4,311,050 | 1/1942 | Bessman .......................... 206/303 |
| 4,466,581 | 8/1984 | Hill .................................. 242/96 |
| 4,582,196 | 4/1986 | Hughson et al. ................. 206/63.3 |

Primary Examiner—David T. Fidei
Attorney, Agent, or Firm—Ladas & Parry

[57] ABSTRACT

A dispenser for surgical wire has a housing with a cover, the housing having a spirally formed channel therein for receiving guidewire. The housing and cover form an integral cassette. The cassette has an inlet connector through which sterilizing fluid may be injected into the channel and an output port through which the guidewire may be uncoiled from the cassette. A web of the housing is shaped to provide a means of securing a J-shaped tip of the guidewire during transportation so that it does not become unwound inside the cassette.

21 Claims, 3 Drawing Sheets

DISPENSER FOR SURGICAL GUIDEWIRE

BACKGROUND OF THE INVENTION

1. Field of the Invention

This invention relates to a dispenser for surgical guidewire.

2. Description of the Related Art

Surgical guidewire is used by a surgeon to pass through arteries of a human body so as to, for example, guiding and locating arterial catheters. Such guidewire often has a J-shaped leading tip so that by manipulating the guidewires it may be routed through desired arteries when an artery junction is reached. The wire is required to be completely sterile and it is normally delivered to a surgical operating theatre in a polyethylene tube which is coiled and the coils clipped together by polyethylene clips. The wire having the J-shaped tip protrudes from the outer coil of the polyethylene tube and a section of the wire between the J-shaped tip and the wire within the tube is threaded inside a tubular member which is used to straighten the J-shaped tip of the guidewire to enable the wire to be initially inserted into an artery.

The opposite end of the tube from the end through which the J-shaped tip protrudes, i.e. the inside coiled end of the tube, is provided with a connector such as that known as a luer for receiving a sterilising solution such as that known under the trade name of HEPERIN, which also serves to lubricate the wire to facilitate travel in an artery. Usually, surgeons connect a syringe to the connector and infuse the sterilising solution through the length of the tube.

It is normal for the dispenser to be supplied by the manufacturer to a surgeon in a sterilised, medical peel pouch. It will be appreciated that the length of the tube is dependent upon the size of the length of wire inserted therein.

Such a known method of manufacturing the guidewire dispenser is extremely labour-intensive requiring the polyethylene tube to be coiled and clipped together using injection-moulded clips and the moulded luer connector to be connected into the internal end of the coiled tube. The guidewire is then inserted into the assembled dispenser. Such a dispenser is usually produced and stocked for different length and diameter guidewire and because of the many variants it is costly to produce. Moreover the dispenser may be distorted due to misuse.

The present invention invention seeks to at least partially mitigate the foregoing disadvantages.

SUMMARY OF THE INVENTION

According to this invention there is provided a dispenser for surgical guidewire including a housing with a cover, said housing having a spirally formed channel therein for accommodating said guidewire and an outlet aperture from which said guidewire may be uncoiled, said housing and cover together forming a cassette.

Preferably the cassette of this invention is made of a plastics material so as to be rigid in normal use but which may be resiliently deformable.

Advantageously the housing and cover are initially discrete integers which are subsequently connected together by, for example, a male/female connection or a snap-fit connection, and conveniently, before or after the guidewire has been inserted into the cassette, the housing and cover are sealed together by one of welding and heat bonding.

Advantageously the housing is opaque and the cover is transparent so that the guidewire may be seen in the cassette and preferably both housing and cover are formed by moulding.

Preferably an inlet port (known as a luer connection port) is provided in the cassette for permitting a sterilising solution to be injected into said channel.

Advantageously a tubular member is releasably fixed to the cassette in the outlet aperture, an axial passage in said tubular member enabling said guidewire to be transportable therethrough and said tubular member being manually removable from said cassette.

Conveniently the cassette has a securement means arranged to prevent the guidewire, provided in use, from being pushed into the cassette. Preferably the outlet aperture is substantially tangential to the housing and the securement means comprise a portion hinged to said housing which is substantially parallel to said tangent and which is movable between a position arranged to underline said tubular member and an end of said guidewire having a J-shaped tip and another position in which said portion is hinged clear of said J-shaped tip. Advantageously said hinged portion includes a hinged flap parallel to and remote from the hinge securing said portion to said housing, and a latch means for removably securing said flap over said guidewire. Advantageously the flap and said portion are each shaped to closely support said guidewire provided in use.

Advantageously the securement means are provided with a further latch means for securing said portion in said position clear of said J-shaped tip in which position said portion is folded through 180° to lie against the back of said housing. Conveniently the latch means and the further latch means are each snap-fit connections provided in the flap and said portion, and in the portion and said housing respectively.

Advantageously said cassette has a generally rectangular cross-shaped section and said inlet port is formed in a radially enlarged part thereof, a planar surface of said radially enlarged part providing a surface for accommodating a label.

Preferably said part has a radially located frangible plug moulded thereon, said plug when separated from said part being arranged to be fitted into said inlet port.

BRIEF DESCRIPTION OF THE DRAWING

The invention will now be described by way of example with reference to the accompanying drawings in which.

DESCRIPTION OF THE PREFERRED EMBODIMENT

Figure 1:
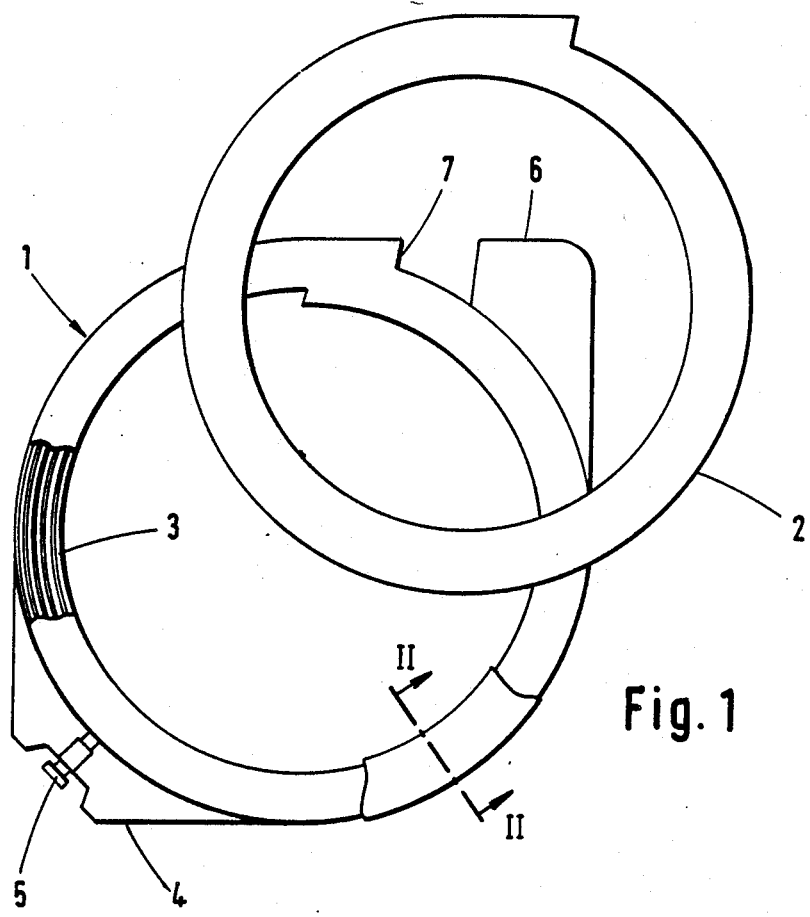
FIG. 1 shows in partial cross-section an exploded view of the dispenser in accordance with this invention.

In the Figures like reference numerals denote like parts.

The dispenser shown in FIG. 1 has a generally circular housing 1 of generally rectangular cross-section formed from opaque polypropylene and a cover 2 also of generally circular configuration made from transparent polystyrene. The housing has a spirally formed open-topped channel 3 shaped to provide five radially disposed apertures for receiving guidewire (not shown) and formed on a web 4 is an inlet connector 5 known as a luer connector. The connector 5 is radially disposed and has a passage extending from the exterior thereof into the channel 3 so that a sterilising solution such as that known under the trade name HEPERIN may be injected via the connector 5 into the channel 3. A further web 6 generally, opposed to the web 4, lies adjacent an output port 7 of the channel 3 and will be described in greater detail later herein.

Figure 2:
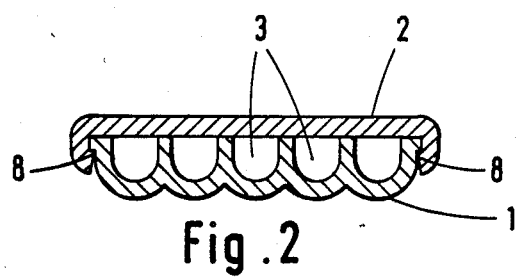
FIG. 2 shows a cross-section along double arrow-headed lines II—II of FIG. 1 in which the cover is located on the housing.

As shown in FIG. 2, the inner and outer peripheral edges of the housing 1 are provided with a lip 8 over which may be snapped a correspondingly shaped part of the cover 2 so that the housing open-topped channels 3 are closed by the cover. The inner and outer peripheral edges of the housing 1 may be sealed to the cover 2 by welding or heat bonding or the like so that when the sterilising solution is injected into the channel 3 it does not escape from the housing and cover combination. It is envisaged however that there may be no sealing between the inner channels and the cover so that solution may pass over the four inner walls of the channel as shown in FIG. 2. The construction thus formed provides a cassette which is rigid in normal use but which may be resiliently deformable and it will be realised that a wire of desired length or diameter may be inserted into the cassette.

It is envisaged that the guidewire will be inserted into the spirally formed channel 3 before the cover 2 is secured in position.

A detail of the web portion 6 is shown in FIGS. 3A–4B.

Figure 3A:
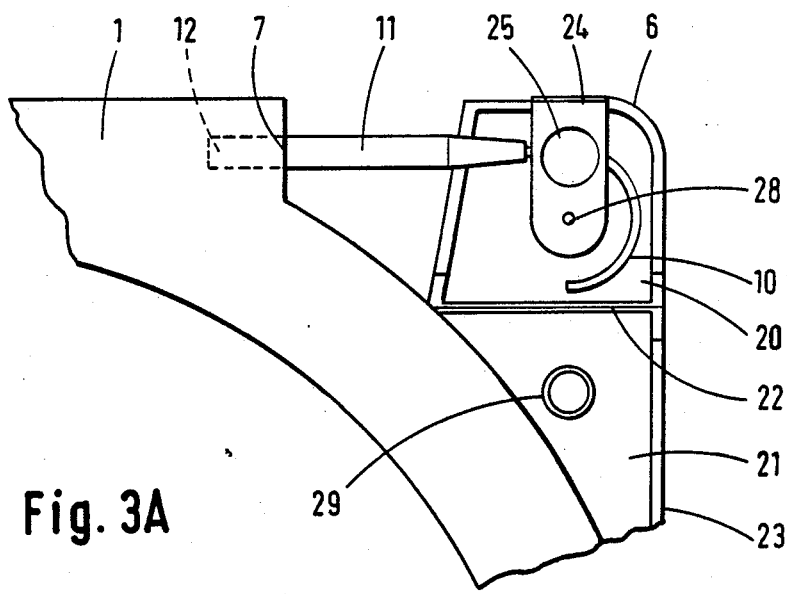
FIG. 3A shows a part of the dispenser for securing the J-shaped tip of the guidewire with the securement device in one position thereof.
Figure 3B:
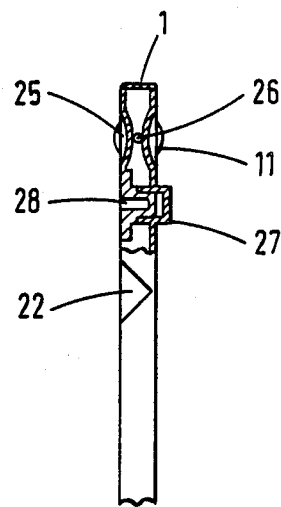
FIG. 3B shows in partial cross-section an orthogonal view to FIG. 3A.

Referring to FIGS. 3A and 3B a guidewire protruding from the outlet 7 in a substantially tangential direction of the housing of the cassette has a J-shaped tip 10 and the portion of the guidewire between the J-shaped tip and the cassette is shrouded inside a tubular member 11, the tubular member 11 being a push fit in a bore 12 circumferentially surrounding the outlet 7. The purpose of the member 11 is that it may be withdrawn from the cassette by a surgeon to straighten the J-shaped tip 10 prior to the surgeon inserting the guidewire into an artery. Once the guidewire has been inserted into an artery the guidewire is completely withdrawn from the cassette and the member 11 slid rearwardly from the guidewire away from the J-shaped tip 10.

The web 6 has a portion 20 connected to a fixed part 21 of the web 6 by a hinge 22 formed by a V-shaped cut-out. The axial length of the hinge 22 is substantially parallel to the tubular member 11. The outer edge of the web 6 has an upstanding wall 23 to protect the J-shaped tip 10. The portion 20 remote from the hinge 22 has a hinged flap 24, the hinge of which is substantially parallel to the hinge 22, and the surfaces of the portion 20 and flap 24 overlying the J-shaped tip 10 are concavely shaped 25, 26 to closely support the guidewire. A depression 27 is formed in the portion 20 and a mating male projection 28 is provided on the flap 24 so that the flap may be predeterminedly secured to the portion 20. The position of the element shown in FIGS. 3A and 3B is a transportation position.

Figure 4A:
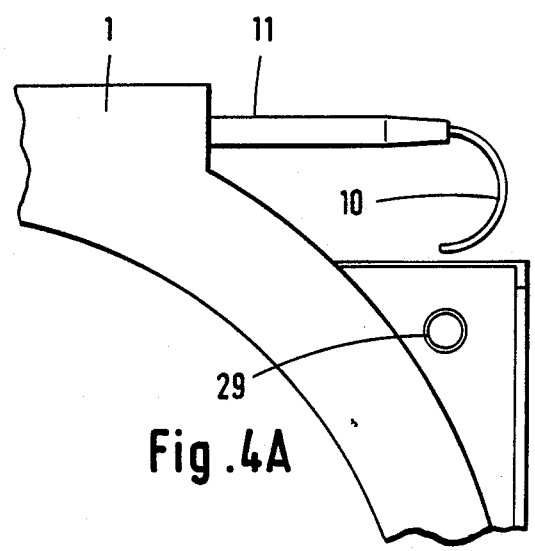
FIG. 4A shows the securement device of FIG. 3A in a different position thereof.
Figure 4B:
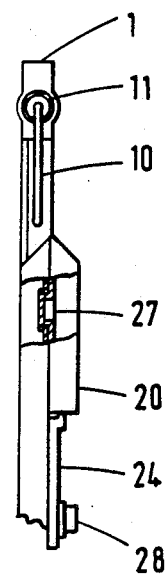
FIG. 4B shows in partial cross-section an orthogonal view of FIG. 4A, and FIGS. 5A and 5B show a frangible plug for the inlet connector.

Referring now to FIGS. 4A and 4B, the male projection 28 has been removed from depression 27 and the portion 20 has been folded through 180° so that the underside projection formed by the depression 27 is located in a hole 29 in the part 21. The portion 20 and flap 24 are thus securely held out of the way so that a surgeon may pull the member 11 from the bore 12 of the housing 1. In this position the guidewire is ready for use by a surgeon.

Figure 5A:
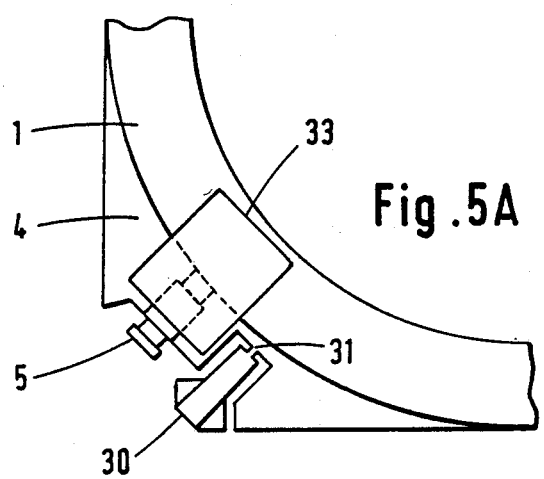
Figure 5B:
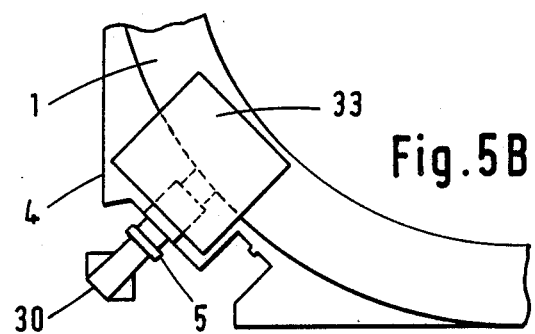

If, as envisaged, the housing and the cover will be injection moulded, it is readily possible to mould a plug 30 which is connected to the web 4 by a flangible element 31, as shown in FIG. 5A. As shown in FIG. 5B, the plug 30 is broken from the element 31 and inserted into the connector 5.

As also shown in FIGS. 5A and 5B the planar surface of the housing formed by the web 4 and the underside of the channel 3 may be used to locate a description label 33 which may contain, for example, a description of the length and diameter of the guidewire.

This invention thus provides a rigid cassette for surgical guidewire which will accommodate varying lengths and diameters of guidewire, an input connection luer integrally formed with the cassette, a member 11 provided for straightening the J-shaped guidewire tip, and provision is made for securing the guidewire during transportation so that it does not become wound inside the cassette. Additionally, the cassette may be constructed to be watertight.

I claim:

1. A dispenser for surgical guide wire including a generally circular housing with a cover therefor, said housing and cover forming a cassette, said housing having a spirally formed channel therein for accommodating said guide wire, an outlet aperture of said cassette disposed substantially tangentially to the housing, from which aperture said guide wire may be uncoiled, a tubular member releasably fixed to said outlet aperture and protruding therefrom, an axial passage in said tubular member enabling said guide wire to be transportable therethrough, and said tubular member being manually removable from said cassette.

2. A dispenser for surgical guidewire including a generally circular housing with a cover therefor, said housing and cover together forming a cassette, said housing having a spirally formed channel therein for accommodating said guide wire, an outlet aperture of said cassette disposed substantially tangentially to the housing, from which aperture said guide wire may be uncoiled, and a securement means for preventing the guide wire, provided in use, from being pushed into the cassette, said securement means comprising a hinged member hinged to said housing and which is movable between a first position arranged to underlie an end of said guide wire having a J-shaped tip, and another position in which said hinged member is hinged clear of said J-shaped tip.

3. A dispenser as claimed in claim 1 wherein the cassette is made of a plastics material so as to be rigid in normal use but which may be resiliently deformable.

4. A dispenser as claimed in claim 3 wherein the housing and cover are initially discrete integers which are subsequently connected together.

5. A dispenser as claimed in claim 4 wherein the housing and cover are sealed together by one of welding and heat bonding.

6. A dispenser as claimed in claim 1 wherein the housing is opaque and the cover is transparent so that the guidewire may be seen in the cassette.

7. A dispenser as claimed in claim 1 wherein both housing and cover are formed by moulding.

8. A dispenser as claimed in claim 1 wherein an inlet port is provided in the cassette for permitting a sterilising solution to be injected into said channel.

9. A dispenser as claimed in claim 1 wherein the cassette has a securement means arranged to prevent the guidewire, provided in use, from being pushed into the cassette.

10. A dispenser as claimed in claim 9 wherein the housing is generally circular and the outlet aperture is substantially tangential to the housing, and the securement means comprise a member secured to said housing by a hinge which hinge has an axis of rotation which is substantially parallel to said tangent and which member is movable between a position arranged to underlie said tubular member and an end of said guidewire having a J-shaped tip, and another position in which said member is hinged clear of said J-shaped tip.

11. A dispenser as claimed in claim 10 wherein said hinged member includes a hinged flap parallel to and remote from the hinge securing said hinged member to said housing, and a latch means for removably securing said flap over said guidewire.

12. A dispenser as claimed in claim 11 wherein the securement means are provided with a further latch means for securing said hinged member in said position clear of said J-shaped tip in which position said hinged member is folded through 180° to lie against the back of said housing.

13. A dispenser as claimed in claim 12 wherein the latch means and the further latch means are each snap-fit connections provided in the flap and said hinged member, and in the hinged member and said housing respectively.

14. A dispenser for surgical guide wire as claimed in claim 2 wherein a tubular member is releasably fixed to the outlet aperture and protrudes therefrom, an axial passage in said tubular member enabling said guide wire to be transportable therethrough and said tubular member being manually removable from said cassette, said tubular member being arranged to overlie said hinged member in the first position of said hinged member.

15. A dispenser as claimed in claim 2 wherein said hinge has an axis of rotation which is approximately parallel to the tangent of said housing.

16. A dispenser as claimed in claim 15 wherein said hinged member includes a hinged flap parallel to and remote from the hinge securing said hinged member to said housing, and a latch means for removably securing said flap over said guidewire.

17. A dispenser as claimed in claim 16 wherein the securement means are provided with a further latch means for securing said hinged member in said another position clear of said J-shaped tip in which position said hinged member is folded through 180° to lie against the back of said housing.

18. A dispenser as claimed in claim 17 wherein the latch means and the further latch means are each snap-fit connections provided in the flap and said hinged member, and in the hinged member and said housing respectively.

19. A dispenser as claimed in claim 2 wherein the housing and cover are initially discrete integers which are subsequently connected together.

20. A dispenser as claimed in claim 2 wherein the housing is opaque and the cover is transparent so that the guide wire may be seen in the cassette.

21. A dispenser as claimed in claim 2 wherein an inlet port is provided in the cassette for permitting a sterilising solution to be injected into said channel.

* * * * *